(12) United States Patent
Kataoka et al.

(10) Patent No.: US 7,585,973 B2
(45) Date of Patent: Sep. 8, 2009

(54) PROCESS FOR PRODUCING FOLIC ACID DERIVATIVES

(75) Inventors: Kazunori Kataoka, Tokyo (JP); Yoshitsugu Akiyama, Tokyo (JP)

(73) Assignee: Japan Science and Technology Agency, Saitama (JP)

( * ) Notice: Subject to any disclaimer, the term of this patent is extended or adjusted under 35 U.S.C. 154(b) by 0 days.

(21) Appl. No.: 10/594,214

(22) PCT Filed: Mar. 25, 2005

(86) PCT No.: PCT/JP2005/006416

§ 371 (c)(1),
(2), (4) Date: Sep. 26, 2006

(87) PCT Pub. No.: WO2005/092902

PCT Pub. Date: Oct. 6, 2005

(65) Prior Publication Data

US 2007/0142387 A1    Jun. 21, 2007

(30) Foreign Application Priority Data

Mar. 26, 2004 (JP) .............................. 2004-092973

(51) Int. Cl.
*C07F 7/10* (2006.01)
*C07D 475/04* (2006.01)
(52) U.S. Cl. ....................................... 544/229; 544/258
(58) Field of Classification Search ................. 544/229, 544/258
See application file for complete search history.

(56) References Cited

FOREIGN PATENT DOCUMENTS

WO     02/085908     10/2002

OTHER PUBLICATIONS

Robert J. Lee et al., "*Delivery of Liposomes into Cultured KB Cells via Folate Receptor-mediated Endocytosis*", The Journal of Biochemical Chemistry, vol. 269, No. 5, pp. 3198-3204 (1994).

Susan Wang et al. "*Delivery of antisense oligodeoxyribonucleotides against the human epidermal growth factor receptor into cultured KB cells with liposomes conjugated to folate via polyethylene glycol*", Proc. Natl. Acad. Sci. USA, vol. 92, pp. 3318-3322 (1995).

Jin Luo et al., "*Efficient Syntheses of Pyrofolic Acid and Pteroyl Azide, Reagents for the Production of Carboxyl-Differentiated Derivatives of Folic Acid*", J. Am. Chem. Soc., vol. 119, pp. 10004-10013 (1997).

Makoto Nomura et al., "*Development of an Efficient Intermediate, α-[2-(Trimethylsily)ethoxy]-2-N-[2-(trimethylsilyl)ethoxycarbonyl] folic Acid, for the Synthesis of Folate (γ)-Coniugates, and Its Application to the Synthesis of Folate-Nucleoside Coniugates*", J. Org. Chem., vol. 65, pp. 5016-5021 (2000).

*Primary Examiner*—Mark L Berch
*Assistant Examiner*—Cecilia M Jaisle
(74) *Attorney, Agent, or Firm*—Wenderoth, Lind & Ponack, LLP.

(57) ABSTRACT

This invention provides a process for efficient production of folic acid derivatives suitable for forming conjugates of anti-cancer drug with folic acid. It discloses a process comprising a step of reacting 2-amino-protected pteroylimidazole with γ-lower alkyl glutamate; and a step of reacting the resulting product with an amino compound having a reactive group which is readily reactable with a functional group of the drug.

7 Claims, No Drawings

PROCESS FOR PRODUCING FOLIC ACID DERIVATIVES

TECHNICAL FIELD

This invention relates to a process for producing folic acid derivatives, in particular, folic acid derivatives suitable for forming conjugates with carcinostatic, and to synthetic intermediate products therefor.

BACKGROUND ART

Accompanying recent remarkable progress in molecular biology, various mechanisms of diseases are being clarified on molecular level, and chemotherapy of cancer has entered upon a new stage. That is, therapy method specified for each individual patient, which is referred to as tailor-made therapy, is in demand, and to meet that demand, it is essential to establish drug design aiming at alleviation of side effect based on clarification of molecular theoretical mechanisms or methodology for drug administration. Generally chemotherapy using carcinostatic or anticancer agents is known as a therapeutic method indispensable where radiotherapy achieves only insufficient effect or where operation cannot be applied as in the case of leukemia.

However, under the current status, cancer chemotherapy is subject to many problems compared to the success in antibiotic therapy represented by penicillin and streptomycin. The greatest reason is that the most of anticancer drugs possess potent toxicity to human body and hence attempts to improve the therapeutic effect by increasing administration doses accompany undesirable side effect, which sets a limit to pharmacotherapy. Under the circumstances, an important point is how to reduce toxicity of anticancer drugs themselves and to promote the therapeutic effect. It is the recent tendency in chemotherapy of cancer developed from the foregoing background that drug targeting aiming at improvement in selectivity of anticancer drugs for target cancer cells is gathering attention.

Folic acid is a member of vitamin B group known as having various physiological activities, which is transported into the cells via the mechanisms called endocytosis or potocytosis mediated by folic acid receptors which are present at the cell surfaces. Hence, if a drug can be bonded with folic acid (formation of folic acid-drug conjugate), positive transport of the drug into the cells via these mechanisms would become possible. Furthermore, it is known that the receptors which recognize folic acid are excessively expressed in cancer cells, and folic acid-drug conjugates are expected to be capable of targeting cancer cells. For example, systems in which folic acid is bound to doxorubicin (DOX, trivial name: adriamycin) or antisense oligodeoxynucleotide (ODN) have already been under investigation and their drug targeting effects are demonstrated (e.g., see the later-identified non-patent documents 1 and 2).

Thus, biological approach using folic acid involves many aspects of high interest, and importance of such folic acid derivatives is widely recognized. Whereas, differing from those conjugates disclosed in the non-patent documents 1 and 2, a number of problems have been pointed out in respect of syntheses of such conjugates heretofore obtained by direct covalent bonding of folic acid with drug. Namely, in most cases covalent bonding of folic acid with drug is conducted with use of a condensing agent such as DCC, and the products are frequently obtained as α- and γ-carboxylate mixtures, and it is very difficult to purify the aimed compound alone as contained in the mixtures. Furthermore, alpha-folic acid derivatives are considered to be entirely meaningless for application in biochemical field, because they have no ability to recognize receptors. While a number of synthesis methods of folic acid derivatives containing γ-carboxylate alone were reported, they generally involve long reaction steps and lack versatility.

Of these, production methods promising to a certain extent also are proposed. For example, in one of them pteroylazide, which was formed from pteroic acid corresponding to the pteroyl moiety as a part of folic acid structure gave folate γ-methyl ester as a key intermediate, through the reaction with γ-methyl glutamate. The intermediate thus obtained was subsequently reacted with ethylenediamine, followed by the conjugation with tumor-specific metal binding ligand (DTPA) via the free amino groups at the ethylenediamine terminal. The literature disclosing the above method also disclosed the compounds obtained by the same method (see, for example, later-identified non-patent document 3).

However, these production methods require many reaction stages before obtaining the key intermediate, and the key intermediate itself is almost insoluble in organic solvents customarily used in organic synthesis reactions. On the other hand, Nomura, M. et al. first pointed out not only the low solubility of the key intermediate in an organic solvent but also the relatively low reactivity between γ-methyl ester moiety with nucleophilic agent, and then proposed a method for obtaining an intermediate product corresponding to the key intermediate, which comprises first protecting the 2-amino group of pteridine ring in pteroic acid with oleophilic group, then converting its carboxyl group to imidazolide, and reacting the imidazolide with a glutamic acid derivative in which γ-carboxyl group of glutamic acid is retained in free state and α-carboxyl group is protected with oleophilic group (see, for example, later-identified non-patent document 4).

Nomura, et al. obtained with use of a condensing agent, a conjugate whose covalent bond is formed between free γ-carboxyl group of such an intermediate and amino group of a drug. However, multi-stage steps are required for obtaining the glutamic acid derivative in which γ-carboxyl group is maintained in free state and α-carboxyl group is protected with an oleophilic group.

List of Cited Documents

Non-patent document 1: Lee, R. J. et al., J. Boil. Chem. 1994, 269, 3198-3204

Non-patent document 2: Wang, S. et al., Proc. Natl. Acad. Sci. U.S.A. 1995, 92, 3318-3322

Non-patent document 3: Luo, J. et al., J. Am. Chem. Soc. 1997, 119, 10004-10013

Non-patent document 4: Nomura, M. et. al., J. Org. Chem. 2000, 65, 5016-5021

DISCLOSURE OF THE INVENTION

It has been desired to provide a method which can selectively introduce intended reactive group into γ-carboxyl moiety only of folic acid, through shorter reaction steps compared to above-described conventional methods. This invention aims at solving the problems existing in those conventional methods, and providing a novel process for producing γ-reactive folate derivatives by shorter reaction steps.

As aforesaid, folate γ-methyl ester which is the key intermediate disclosed in the non-patent document 3 has low solubility in organic solvent and also low reactivity with nucleophilic agent, as indicated in the non-patent document 4 (see, in particular, p. 5016, rt. col., L. 2 from the bottom—p. 5017, lt. col., L. 4). We discovered that γ-lower alkyl esters of 2-amino-protected folic acid which is obtained from imidazolide of 2-amino-protected pteroic acid, a precursor of the compound corresponding to the key intermediate as disclosed in the non-patent document 4, are soluble in organic solvents customarily used in organic synthesis reactions even though their α-carboxyl groups are free, contrary to the suggestion by Nomura, et at. We also discovered, furthermore, that the amino compound residue could be readily covalently bonded with folic acid through a reaction between the ester groups with the amino compounds.

Accordingly, the present invention provides, as a means for solving the foregoing problems, a process for producing folic acid derivatives which comprises:

a) a step of reacting an imidazolide represented by a formula (A):

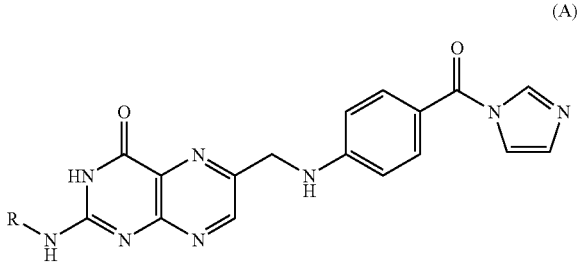

(A)

(in the formula, R stands for a protective group of amino group) with γ-lower alkyl L-glutamate in an organic solvent in the presence of a base to form a γ-lower alkyl 2-amino-protected folate which is represented by a formula (B):

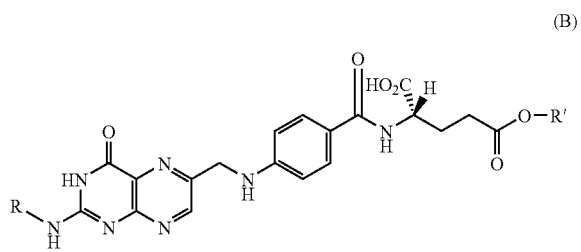

(B)

(in the formula, R has the same signification to its definition given as to the formula (A), and R' stands for a lower alkyl); and b) a step of reacting a γ-lower alkyl 2-amino-protected folate represented by the formula (B) with an amine compound of a formula (C):

R"-L-NH$_2$           (C)

{in the formula, R" stands for a reactive group readily reactable with a functional group of an organic compound, and L stands for a linkage, $C_1$-$C_5$ alkylene or an oligo- or poly-(oxyalkylene) of a formula, —(CH$_2$CH(R$^C$)—O—)$_n$CH$_2$CH(R$^C$)—

(in which R$^C$ stands for hydrogen or methyl, and n is an integer of 1-10,000)} to produce a folic acid derivative of a formula (D):

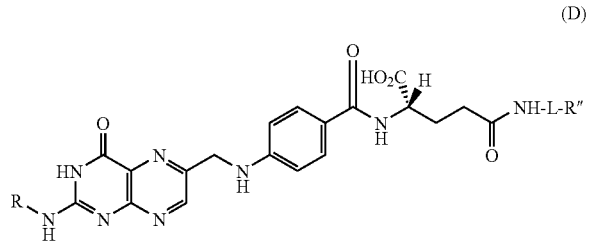

(D)

(in the formula, R has the same signification to its definition given as to the formula (A), and L and R" have the same significations to those as defined as to the formula (C)).

So far as we are aware of, the compounds represented by the above formula (B) in which the 2-amino group on the pteridine ring is protected and the γ-carboxyl group is a lower alkyl ester group are disclosed in no prior art literature. Therefore, these compounds also are provided as one embodiment of the present invention.

Hereinafter specific embodiments of the present invention are explained.

The term, "lower alkyl" group, used in relation to the present invention signifies branched or straight chain alkyl groups having 1-6 carbon atoms ("$C_1$-$C_6$ alkyl"), specific examples including methyl, ethyl, n-propyl, iso-propyl, n-butyl, tert-butyl, n-hexyl and so on.

The amino-protective group (R) in the formula (A) is a group readily removable depending on necessity, which can be of a great variety including, for example, protective groups used for protecting amino groups of amino acids in the occasions of peptide syntheses (e.g., benzyloxycarbonyl, t-butoxycarbonyl, acetyl and the like), trifluoro trifluoromethanesulfonyl, p-toluenesulfonyl, organic silyl residues and the like. Preferred (R) are those represented by the following formula,

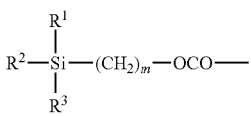

(in the formula, $R^1$, $R^2$ and $R^3$ each independently stands for lower alkyl, and m stands for an integer of 1-4).

As specific examples, trimethylsilylmethoxycarbonyl, 2-trimethylsilylethoxycarbonyl, 3-trimethylsilylpropoxycarbonyl, 2-ethyldimethylsilylethoxycarbonyl, 2-tert-dimethylsilylethoxycarbonyl, triethylsilylmethoxycarbonyl, 2-triethylsilylethoxycarbonyl and the like can be named.

Compounds of the formula (A) having such amino-protective groups (in particular, trimethylsilylethoxycarbonyl) can be obtained, as disclosed in the non-patent document 4, by reaction of protein acid with N,N'-carbonyldiimidazole (CDI) and 2-(trimethylsilyl)ethanol, or by methods analogous thereto. The step a) according to the present invention is conducted by dissolving a compound of the formula (A) in an organic solvent, preferably a polar aprotic solvent, for example, dimethylsulfoxide (DMSO), N,N'-dimethylformamide (DMF), N-methylpyrrolidone or the like, and reacting the same with γ-lower alkyl glutamate in the presence of base, preferably an organic strong base, for example, N-methyl-1,5,9-triazabicyclo[4.4.0]decene (MTBD), 1,8-diazabicyclo[5.4.0]undec-7-ene (DBU) or the like. The optimum reaction conditions such as temperature and time vary depending on such factors as the kind of used base, while the priority in selecting the temperature is placed on prevention of recemization of glutamic acid. It is normally suitable to carry out the reaction at room temperature for around 20 hours. Thus a compound of the formula (B) can be obtained at high yield.

The step b) is the stage for introducing reactive group(s) capable of forming covalent bond with drug, in particular, anticancer drug (which is functionalized where necessary). In this stage a compound of the formula (B) is reacted with an amino compound represented by the formula (C),

R"-L-NH$_2$           (C)

in an organic solvent (preferably the solvent used in above step a)) or in the absence of any solvent (in particular, where the amino compound to be reacted with the compound of the formula (B) is liquid at room temperature), to provide a compound represented by the formula (D) in which the alkoxy group in the γ-lower alkyl ester is substituted with R"-L-NH₂— group in the compound of the formula (C).

The reactive group R" in the formula (C) which is readily reactable with a functional group in organic compound, in particular, functional group of anticancer drug (including those functional groups which have been introduced into the original structures of anticancer drug, where necessary, to meet the object of the present invention or to enable the drug to participate in the reaction according to the present invention), signifies such a group capable of forming a covalent bond by the reaction with the functional group of organic compound, without any adverse effect on the ability of folic acid to bind to the folic acid-recognizing receptors which are expressed in, for example, cancer cells. As such reactive groups,
(i) amino group (—NH₂),
(ii) substituted disulfide group, e.g.,

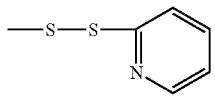

(iii) acetylene group

and
(iv) azide group (—N₃)

can be named. Such a reactive group is either directly bonded with an amino group of a compound of the formula (C), or bonded to the amino group via a linkage (L): $C_1$-$C_5$ alkylene, e.g., methylene, di-, tri-, tetra- or penta-(methylene); or an oligo- or poly-(oxyalkylene) chain represented by the formula,

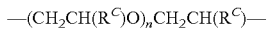

(in the formula, $R^C$ stands for hydrogen or methyl, and n is an integer of 1-10,000).

The compound of the formula (D) having such a reactive group can react with the functional group, which is reactable with the reactive group in drug, in particular, an anticancer drug, under mild reaction conditions known per se, to form a covalent bond and provide a folic acid-drug conjugate.

Although in no way limitative sense, those reactive groups (i)-(iv) can react with the following functional groups, respectively, to form covalent bonds.

(i) In case of amino group, folic acid and the drug can be easily bound via the carbonyl at 13-carbon of doxorubicin and Schiff base. What should be noted is that the Schiff base which is formed with use of hydrazide group cleaves the bond again under acidic condition within endosomes (see, for example, Angew. Chem. Int. Ed., 42, 4640 (2003)). Generally, one of the problems encountered when a folic acid-drug conjugate formed by strong covalent bond is taken into the cells is that the drug is discharged from the cells once again following the receptor recovery mechanism from intracellular endosomes. If the folic acid and the drug can be cleaved within intracellular endosomes, intended medicinal effect can be further increased. Hence, where folic acid is bound to doxorubicin via the Schiff base formed of the carbonyl group and amino group of hydrazide and designed to be pH-responsive, not only the folic acid-doxorubicin conjugate is energy-dependently taken into the cells at high efficiency via the folic acid receptors excessively expressed in cancer cells, but also the Schiff base cleaves during migration of the conjugate from the intracellular endosomes to lysosomes, enabling release of the doxorubicin from the folic acid receptors. Thus the doxorubicin is not discharged to outside the cells when the receptors are recovered to the cell surface, and achievement of effective intracellular drug release can be expected. Again, if appropriate, a drug can be converted in advance to an active ester functionalized by succinimidylation or the like, to form an amido bond.

(ii) In case of substituted disulfide group, thiol group is introduced into a part of the object drug in advance by a means known per se where necessary, to form a disulfide bond accompanying cleavage of the substituted disulfide group and the thiol group.

(iii) In case of acetylene group, azide group is introduced into a part of the object drug in advance by a means known per se where necessary, and a folic acid-drug conjugate can be formed via the triazole ring formation by "Huisegen 1,3-dipolar cycloadditions" between the acetylene group and azide group. (Concerning the dipolar cycloaddition reaction, see, for example, Angew. Chem., 2002, 114, p. 2708-2711.)

(iv) In case of azide group, acetylene group is introduced into a part of the object drug in advance by a means known per se where necessary, and a folic acid-drug conjugate can be formed in the manner similar to (iii) above.

Thus, according to the present invention, production processes for making folic acid derivatives suitable for forming conjugates of drug and folic acid are provided. Also the products of the above step a) and step b) can be isolated by per se known means such as chromatography, solvent extraction, recrystallization and the like.

Hereinafter the present invention is explained referring to specific examples, it being understood that they are in no way intended to limit the scope of the present invention.

PRODUCTION EXAMPLE 1 (REFERENTIAL EXAMPLE)

Synthesis of 1-[2-N-[2-(trimethylsilyl)ethoxycarbonyl]pteroyl]-imidazole

To a mixture of 3.0 g of pteroic acid and 5.35 mL of triethylamine (TEA), 6.24 g of CDI as dissolved in 50 mL of DMSO was added and reacted at room temperature for 3.5 hours. To the reaction solution 2-(trimethylsilyl)ethanol (9.63 mL) was added, followed by further 5 hours' reaction at room temperature. The reaction solution was added dropwise into water (10 mL)-acetic acid (0.32 mL) and dimethyl ether (6.4 mL), vigorously stirred for a few minutes, and recovered as solid by suction filtration. The solid product was purified by column chromatography (silica gel column: eluent; 10% methanol in chloroform) and dried under reduced pressure to finally give 2.67 g (yield=54.8%) of aimed compound.

PRODUCTION EXAMPLE 2 (WORKING EXAMPLE)

Synthesis of γ-methyl 2-N-[2-(trimethylsilyl)ethoxycarbonyl]-folate

Into 0.477 g (2.96 mmols) of γ-methyl glutamate, a solution of 1.0 g (1.97 mmols) of 1-[2-N-[2-(trimethylsilyl) ethoxycarbonyl]-pteroyl]imidazole and 0.7 mL (4.8 mmols) of MTBD in 10 mL of DMSO was dropped and reacted at room temperature for 21 hours. As the purification treatment, the reaction solution was added dropwise to aqueous acetic acid (1M, 30 mL)-methanol (15 mL) and CHCl₃ (30 mL), and the organic layer was washed with acetic acid (1M)-methanol (1:1, 20 mL) and water-methanol (2:1, 30 mL, twice), then dehydrated over Na₂SO₄, filtered, and the solvent was distilled off. Finally the residue was washed with CHCl₃-diethyl ether to give 1.05 g (yield: 88.5%) of the aimed compound. This compound was identified to be the aimed compound by ¹HNMR measurement (one of the peaks (7.1 ppm) attributable to imidazole group disappeared completely and newly a peak (3.6 ppm) attributable to the methyl glutamate group was observed).

PRODUCTION EXAMPLE 3 (WORKING EXAMPLE)

Synthesis of folic acid γ-hydradide

γ-Methyl 2-N-[2-(trimethylsilyl)ethoxycarbonyl]folate (0.21 g) was dissolved in 10 mL of anhydrous hydrazine and reacted at 50° C. for 3 hours. After termination of the reaction, the solvent was removed under reduced pressure, and the residue was re-dissolved in 10 mL of aqueous hydrochloric acid (pH 1.0), stirred for an hour at room temperature, neutralized with aqueous NaOH solution and then lyophilized. The lyophilized product was re-dissolved in pure water and centrifuged twice to be desalted. Finally, the aimed compound was lyophilized and recovered as a yellow powder.

INDUSTRIAL APPLICABILITY

As above, the method of the present invention can provide folic acid derivatives for forming folic acid-drug conjugates with drug, specifically, anti-cancer agents. The invention is useful in the field of pharmaceutical preparations.

The invention claimed is:

1. A process for producing a folic acid-amide compound comprising: a) reacting an imidazolide represented by the following formula (A):

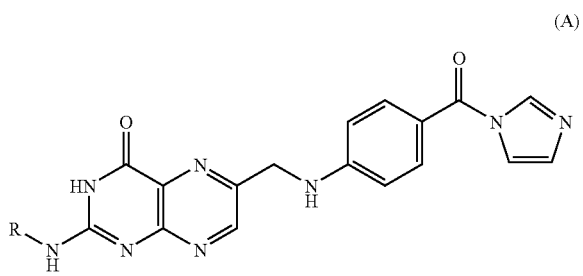

(A)

wherein R represents a protecting group for amino acid and is an amino acid protecting group used in peptide synthesis, with γ-lower alkyl L-glutamate in an organic solvent in the presence of an organic base to form a γ-lower alkyl 2-amino-protected folate which is represented by the following formula (B):

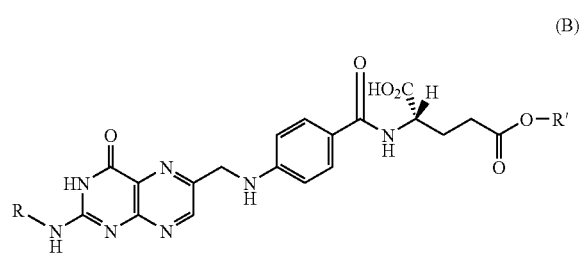

(B)

wherein R has the same definition as in formula (A), and R' represents a lower alkyl; and b) reacting a γ-lower alkyl 2-amino-protected folate represented by the formula (B) with an amine compound of the following formula (C):

R''-L-NH₂     (C)

wherein R'' represents amino,

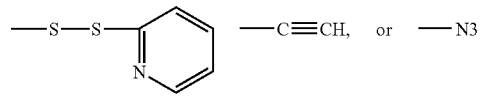

and

L represents a valence bond, $C_1$-$C_5$ alkylene or an oligo- or poly-(oxyalkylene) of the following formula,

—(CH₂CH(R^C)—O—)ₙCH₂CH(R^C)— wherein $R^C$ represents hydrogen or methyl, and n is an integer of from 1-10,000 to produce a folic acid-amide compound of the following formula (D):

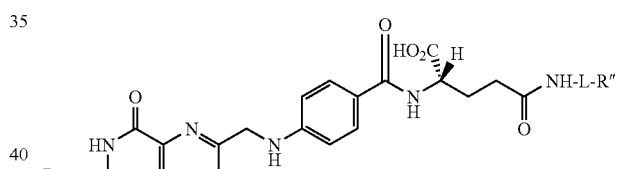

(D)

wherein R has the same definition as in the above formula (A), and L and R'' have the same definitions as in the above formula (C).

2. The process according to claim 1, wherein R in the formula (A) is a group represented by the following formula,

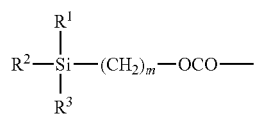

wherein $R^1$, $R^2$ and $R^3$ each independently represents lower alkyl, and m represents an integer of from 1-4.

3. A Gamma-lower alkyl 2-amino-protected folate represented by the following formula (B-1):

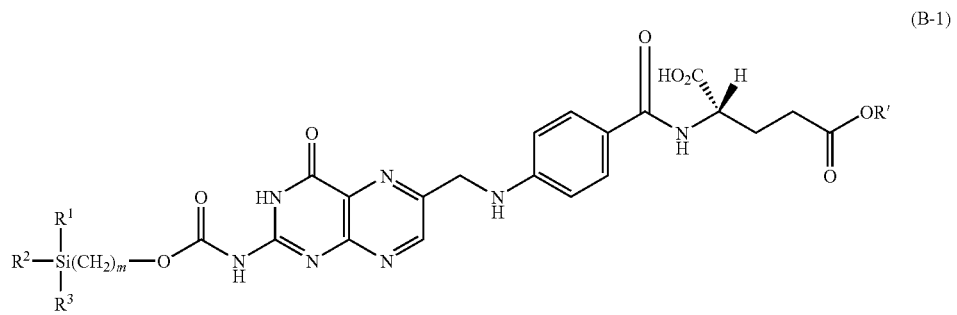

(B-1)

wherein R¹, R² and R³ each independently represents lower alkyl; m represents an integer of 1-4; and R' represents lower alkyl.

4. The process according to claim 1, wherein R represents benzyloxycarbonyl, t-butoxycarbonyl, acetyl, trifluoromethanesulfonyl, or p-toluenesulfonyl.

5. The process according to claim 2, wherein R represents trimethylsilylmethoxycarbonyl, 2-trimethylsilylethoxycarbonyl, 3-trimethylsilylpropoxycarbonyl, 2-ethyldimethylsilylethoxycarbonyl, 2-tert-dimethylsilylethoxycarbonyl, triethylsilylmethoxycarbonyl, or 2-triethylsilylethoxycarbonyl.

6. The process according to claim 1, wherein the organic base is N-methyl-1,5,9-triazabicyclo[4.4.0]decene.

7. The process according to claim 1, wherein the organic base is 1,8-diazabicyclo[5.4.0]undec-7-ene.

* * * * *